United States Patent [19]
Doyle

[11] Patent Number: 5,459,316
[45] Date of Patent: Oct. 17, 1995

[54] IMMERSION PROBE FOR INFRARED INTERNAL REFLECTANCE SPECTROSCOPY

[75] Inventor: Walter M. Doyle, Laguna Beach, Calif.

[73] Assignee: Axiom Analytical, Inc., Irvine, Calif.

[21] Appl. No.: 188,898

[22] Filed: Jan. 31, 1994

[51] Int. Cl.[6] .......................... G01N 21/35; G01N 21/84
[52] U.S. Cl. .................. 250/339.11; 250/339.12; 250/341.2; 250/341.8
[58] Field of Search ................ 356/244; 250/339.11, 250/339.12, 343, 341

[56] References Cited

U.S. PATENT DOCUMENTS

4,812,041  3/1989  Doyle ........................ 356/244
4,835,389  5/1989  Doyle ........................ 250/343
5,051,551  9/1991  Doyle ........................ 250/341

Primary Examiner—Carolyn E. Fields
Attorney, Agent, or Firm—Thomas J. Plante

[57] ABSTRACT

An immersion probe (for powder or liquid) is disclosed comprising an ATR element supported at the bottom of a radiation-confining tube. The ATR element has a sample-entering tip which is either conical (preferably) or roof-top shaped. The ATR element causes entering radiation to be reflected twice by its sample-engaging surfaces, where attenuation due to the sample material occurs. The ATR element also acts as a retroreflector, causing the exiting radiation to follow a path parallel to the entering radiation. In order to avoid spurious results due to reflection by the rear surface of the ATR element, its rear surface is cone shaped or rooftop shaped, using a large apex angle.

13 Claims, 8 Drawing Sheets

FIG. 8b

IMMERSION PROBE FOR INFRARED INTERNAL REFLECTANCE SPECTROSCOPY

BACKGROUND OF THE INVENTION

This invention relates to internal reflectance spectroscopy using an immersion probe to enter a container whose contents are to be analyzed. The analysis is accomplished by attenuated total reflectance (ATR), for which an internal reflectance element (IRE) is used.

Two patents relating to this field of development have been issued to assignees of the present inventor. U.S. Pat. No. 4,835,389 disclosed an IRE at the lower end of a single cylindrical hollow tube. U.S. Pat. No. 5,051,551, assigned to the assignee of this application, disclosed an immersion probe comprising a pair of hollow light pipes which conduct IR radiation to and from an ATR element which may or may not also serve as the retroreflecting element.

The two light pipe design has a distinct performance advantage over the single light pipe design because it obviates the need to use a beamsplitter to separate the incoming and outgoing beams. For any realistic beam divergence, the beams are essentially scrambled by the light pipes. For a given optical aperture, beam splitting results in a loss of at least 50% for both the incoming and outgoing beams, giving a theoretical maximum transmission of 25%.

In spite of the transmission advantage of the two light pipe design, there are important potential applications which require probe diameters too small to be practical with two light pipes. For this reason, the applicant has developed a new probe employing a single light pipe. In doing so, it has been necessary to deal with a problem that was not addressed in U.S. Pat. No. 4,835,389.

SUMMARY OF THE INVENTION

The present invention uses a conical-shaped piece of infrared (IR)-transparent material which serves both as an ATR element and as a retroreflector. The conical (or rooftop-shaped) ATR element is located at the lower (remote) end of a single light pipe tube, which serves as an optical transfer element of an immersion probe.

Because the ATR element has its apex at the remote end of the immersion tube, there are two benefits. The ATR element provides a two-reflection IRE, i.e., the IR light is subject to attenuated reflectance by the sample at two points. And the probe can be readily pushed into a powder sample, because of its pointed (or edged) lower end.

The shape of the upper (nearer) end of the ATR element is designed to prevent, or minimize, undesired back surface reflection of the incoming radiation. Such back surface reflection can give rise to spurious results, because it is stray light in the system. After considering several possible solutions of this problem, the structure disclosed in this application was developed, which is considered an elegant solution.

The ATR element is fabricated with a shallow cone as its rear (or light-entering) surface. The rear surface is designed to reflect light at angles (to the axis of the tube) sufficiently large to cause light reflected from the rear surface of the ATR element to miss the detector collecting optics. A correction is required to preserve retroreflection by the ATR element, but this can be accomplished by modifying the lower (remote) apex angle of the lower conical surface which engages the sample.

The principles underlying the design just described can be applied to a design using a wedged (rooftop) element rather than a cone.

DETAILED DESCRIPTION OF PREFERRED EMBODIMENT

Figure 1:
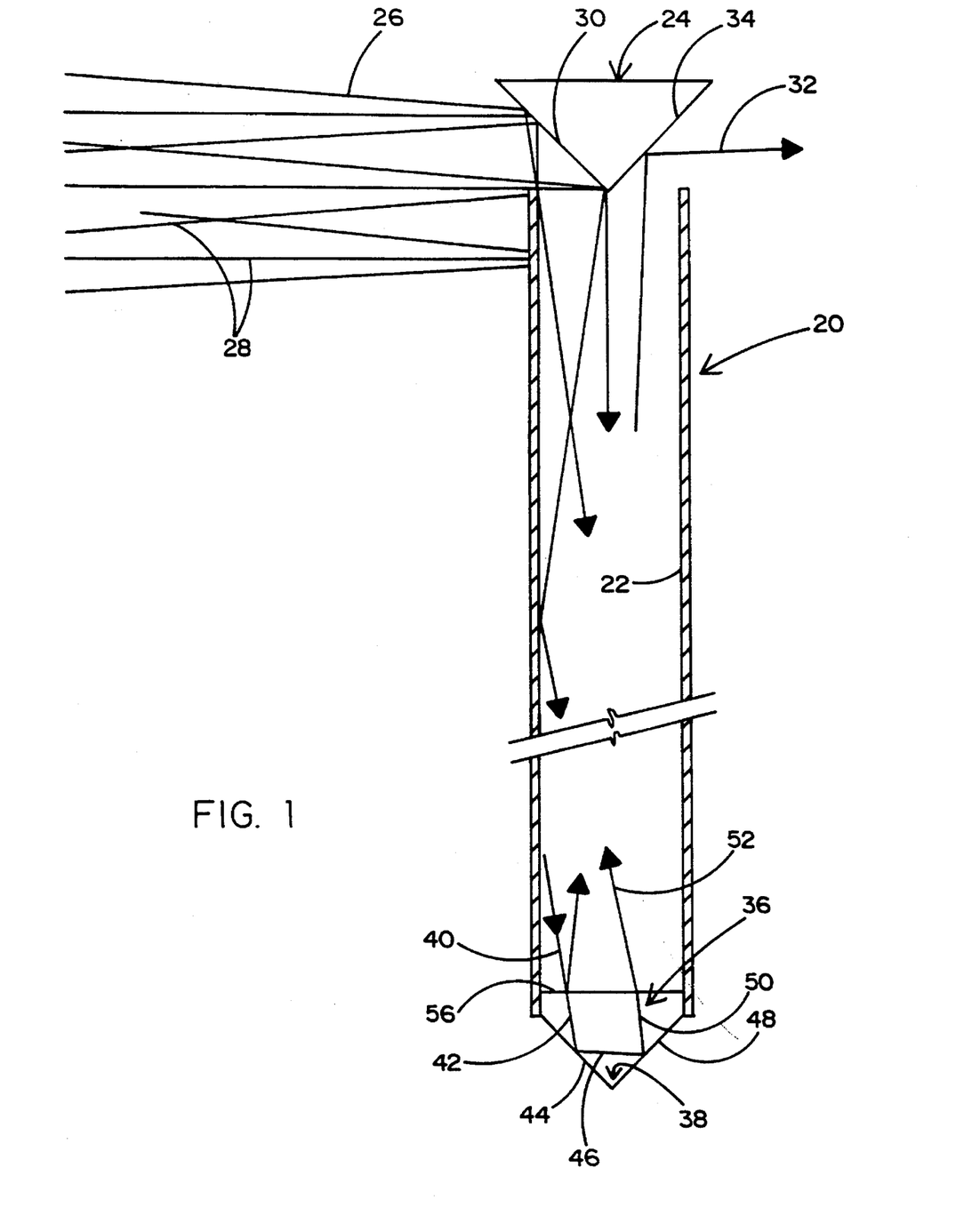
FIG. 1 is a schematic, partly in cross-section, showing a sample-entering probe having at its tip an ATR element.

FIG. 1 shows schematically a single tube probe having at its lower end a conical piece of infrared (IR) transparent material, which serves both as an ATR element and as a retroreflector.

A tube 20, typically 8 mm in diameter, acts as a light-confining enclosure for infrared light (either near or mid infrared), which receives incoming light from a source, and emits post-sample light which is directed to a detector. Preferably, the inner surface 22 of the tube (light pipe) is coated with highly reflective material which causes the maximum amount of radiation to travel in both directions within light pipe 20. Incoming rays from the source may be intercepted by a 90° rooftop-shaped mirror 24, acting as a beamsplitter. The beamsplitter reflects half of the incoming beam (rays 26) into the light pipe. The other half of the incoming beam (rays 28) do not enter the light pipe. Incoming rays 26 are reflected into the light pipe 20 by surface 30 of the beamsplitter. Exiting rays 32 are also divided in half by the beamsplitter. Those reflected from the beamsplitter surface 34 are directed to a detector. Those reflected by beamsplitter surface 30 are lost.

The end of the probe which enters the sample is normally the lower end of the light pipe 20. Mounted in and secured to the lower end of light pipe 20 is a conically shaped piece of IR-transparent material 36 which serves both as an ATR element and as a retroreflector. The apex angle 38 of this element is ideally 90° so that a paraxial ray, traveling parallel to the light pipe (tube) axis, is reflected back on a parallel path. The effect of ATR element 36 on the IR rays is illustrated by an incoming ray path 40, which is deflected slightly as it enters element 36, becoming path 42. It is reflected at surface 44 of element 36, and follows path 46 to be reflected again at surface 48 of element 36. The ray is thus retroreflected to follow return path 50 inside element 36 and return path 52 after leaving element 36.

The reflections at surfaces 44 and 48 are the sample analyzing points of the attenuated total reflectance (ATR)

element. The radiation which is reflected at 44 and 48 is altered by partial absorption (attenuation) in the sample material surrounding the ATR element.

The number of reflection points for certain materials, e.g., many pure organic substances, is ideally two, as in the present disclosure. There are situations where a larger number of attenuation reflections would be preferred. For example, for a solution in which the substance of interest is only, say, 10% of the solution, more than two reflections would be desired. But, where pure, highly concentrated materials are being investigated, two reflections may be optimum, because absorbances which go beyond one absorbance unit (10% transmitting) may lead to non-linear results (and other problems).

As previously stated, a two reflection ATR element also provides the benefit of being a retroreflector, i.e., it causes the light to be returned along a path parallel to the path of the incoming light.

A problem with the design shown in FIG. 1 is that IR radiation reflected from the flat rear surface 56 of the ATR element is essentially stray light. If this reaches the IR detector, it will give rise to spurious results which can be difficult to correct analytically. The effect of this could be reduced by applying an antireflection coating to the offending surface. However, this would be effective only over a restricted wavelength range. More generally effective solutions to the problem are described below.

Figure 2:
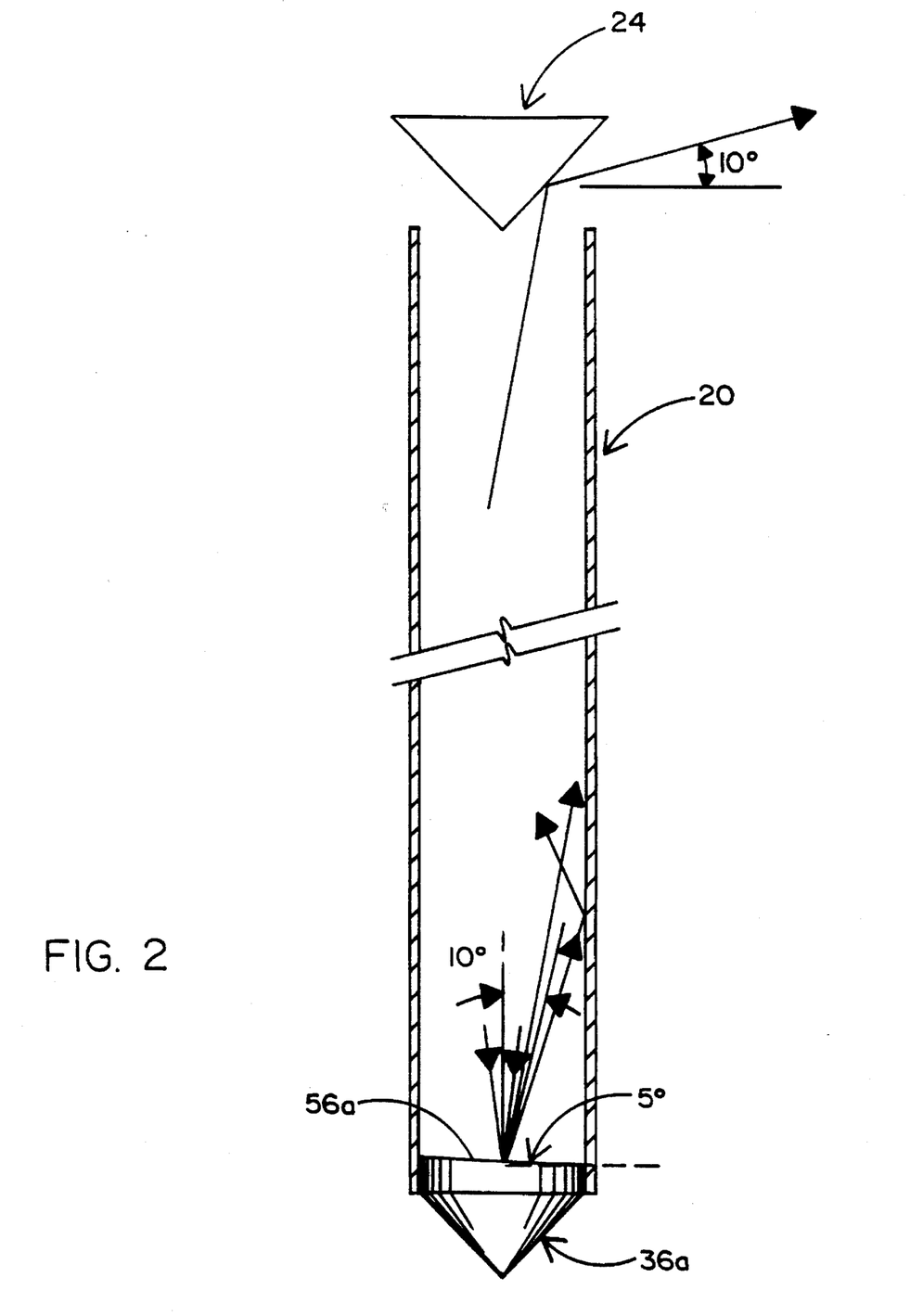
FIG. 2 shows the probe of FIG. 1, in which a design adjustment has been made to remove from the system radiation reflected from the rear surface of the ATR element.

FIG. 2 shows one possible way of eliminating the effects of first surface reflection. The first, or light entry, surface 56a of ATR element 36a can be inclined, as shown, with respect to the axis of the light pipe 20. The figure shows an inclination of 5° from a plane perpendicular to the light pipe axis. With a sufficient inclination of surface 56a, the reflected light from that surface will travel within a range of angles (relative to the axis) large enough so that first surface reflection emerging from the light pipe will miss the detector collecting optics.

Figure 3:
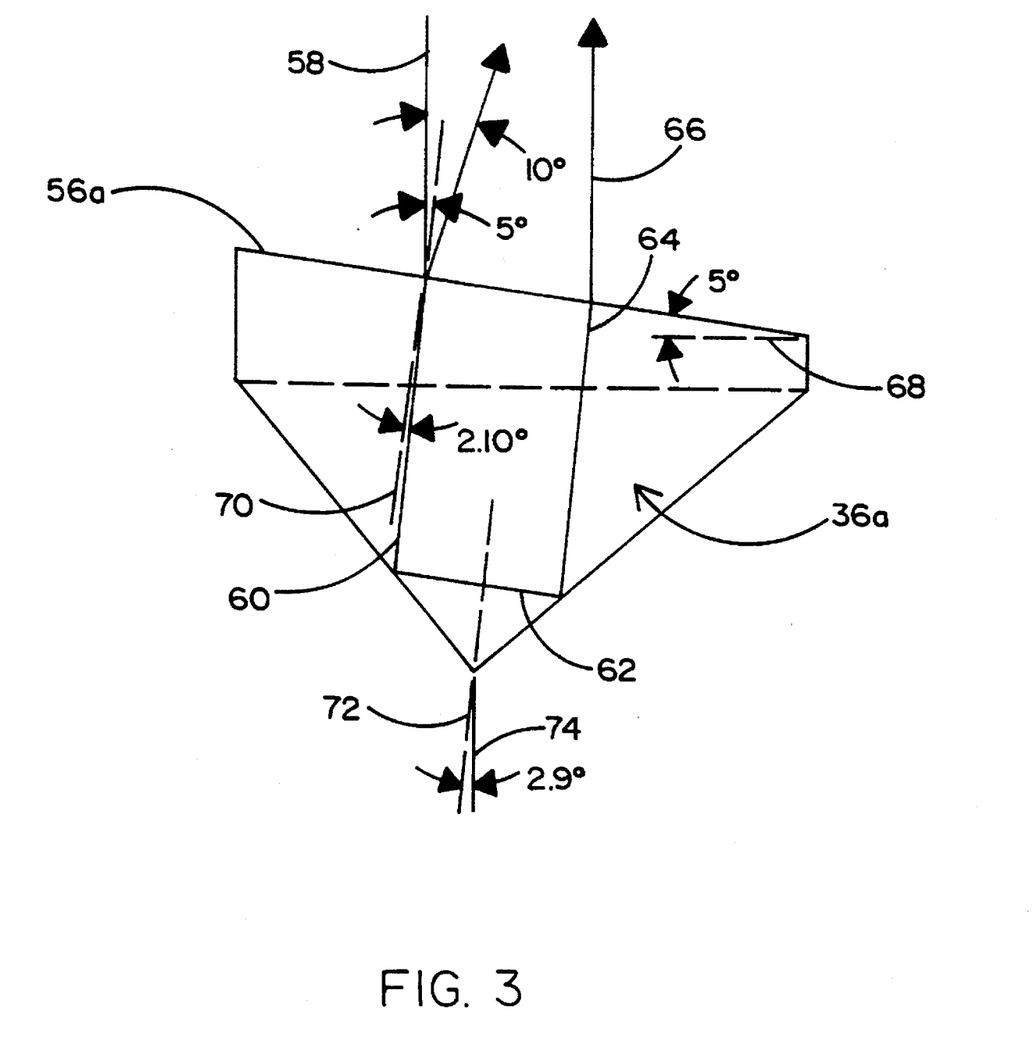
FIG. 3 shows a further design adjustment motivated by a deficiency in the FIG. 2 design.

The concept illustrated in FIG. 2 has a significant drawback. As illustrated in FIG. 3, rays traveling along entering path 58 will be refracted when they enter ATR element 36a, and will then travel along paths 60, 62, 64 and 66. In order to optimize the retroreflecting effect of the lower cone surface of the ATR element, the axis of the cone portion must be tilted so that its axis is parallel to the paraxial rays 60 and 64, after refraction has altered the direction of those rays. This causes the axis of the cone portion of ATR element 36a to be different from the axis of the cylindrical portion of the ATR element. A difficult fabrication problem is created by this axis differential. Also, a skewed ATR tip might cause problems in some applications.

FIG. 3 illustrates the problems just described. Surface 56a is inclined 5° from the perpendicular surface indicated by dashed line 68. Assuming that the ATR element has an index of refraction of 2.4 (e.g., zinc selenide), the angle of refraction will be 2.1°, i.e., the angle between a line 70 perpendicular to surface 56a and the path 60 of ray 58. In order to cause paths 60 and 64 to be parallel (and therefore paths 58 and 66), the axis of rotation (indicated by dashed line 72) of the cone portion of the ATR element is at an angle of 2.9° with the axis of rotation (indicated by line 74) of the cylindrical portion of the ATR element.

Figure 4:
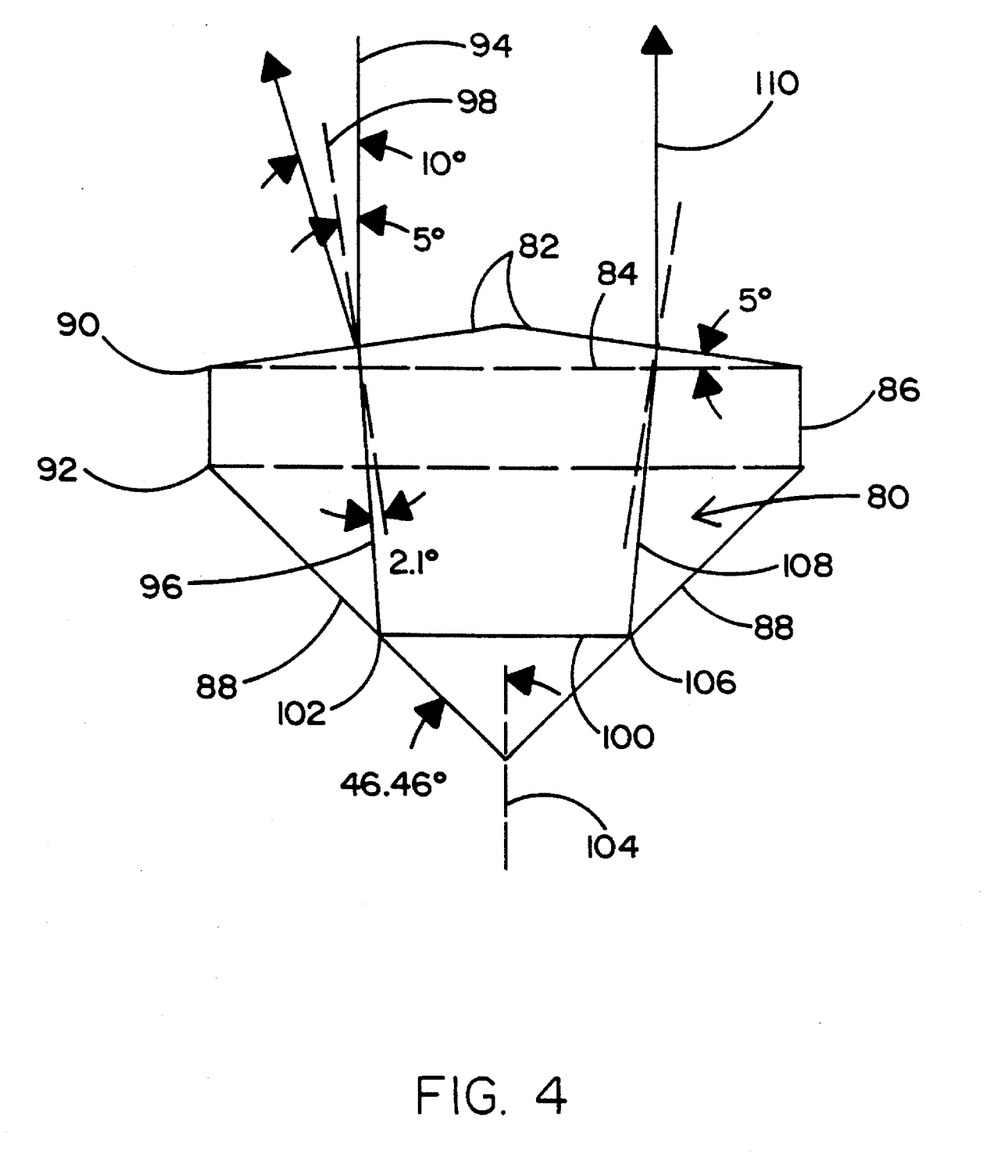
FIG. 4 shows schematically an ATR element which effectively removes the deficiencies of the device in the previous figures, without sacrificing any of the benefits.

The ATR element 80 shown in FIG. 4 provides an elegant solution of the first surface reflection problem, without creating significant manufacturing difficulties. The radiation-entering portion of element 80 has a shallow cone-shaped (of rooftop shaped) surface 82, which provides the desired rear surface inclination without compromising the parallelism of entering and exiting light rays. This shallow cone portion may be formed with a 5° angle between the convex cone sides and the perpendicular plane 84. Because the ATR element preferably has a cylindrical portion 86 between the cone-shaped entering portion 82 and its cone-shaped sample-engaging portion 88, two dashed lines 90 and 92 represent the upper and lower circular edges of the cylindrical portion. The cylindrical portion 86 is desirable because it engages (and is positioned by) the cylindrical inner wall of the light pipe tube.

The dimensions of the ATR element 80 are chosen primarily for ease of fabrication, and secondarily for aesthetic reasons. It is symmetrical around the central axis (axis of rotation) of the incoming beam.

An entering light ray 94 is shown on a path parallel to the axial center of the light pipe. Because the shallow cone 82 has a 5° angle from line 84, the light path 96 after refraction has an angle of 2.1° from a line 98 perpendicular to cone 82, assuming a 2.4 index of refraction of the material of ATR element 80.

In order to provide a horizontal (perpendicular to the light pipe axis) path 100 for the light ray after its reflection from sample-engaging cone surface 88 at point 102, the apex angle of cone 88 needs to be slightly larger than the often-used 90° angle. The angle between line 104 representing the axis of the light pipe (and of the ATR element) and each side of ATR cone 88 is 46.46°. The apex angle of the cone is 92.92°. After reflection at point 106, the light follows path 108 inside the ATR element, and after exiting therefrom, follows path 110 out of the light pipe. Exiting path 110 is parallel to entering path 94.

The light is modulated by sample attenuation at the two points 102 and 106, thus providing the detector with modulated radiation which can be converted into analytical information concerning the sample material.

The principles underlying the double cone concept disclosed in FIG. 4 may also be incorporated in a design having wedge-shaped surfaces as the top and bottom surfaces of the ATR element. A cross-section of such an ATR element would be identical with FIG. 4, except that (a) the junction of lines 82 in the figure would represent the edge of a roof-top rather than the apex of a cone, and (b) the junction of lines 88 would also represent the edge of a roof-top rather than the apex of a cone. U.S. Pat. No. 5,051,551 discusses the light paths created by conical and roof-top retroreflectors (column 10, line 51 to column 11, line 13).

Figure 8A:
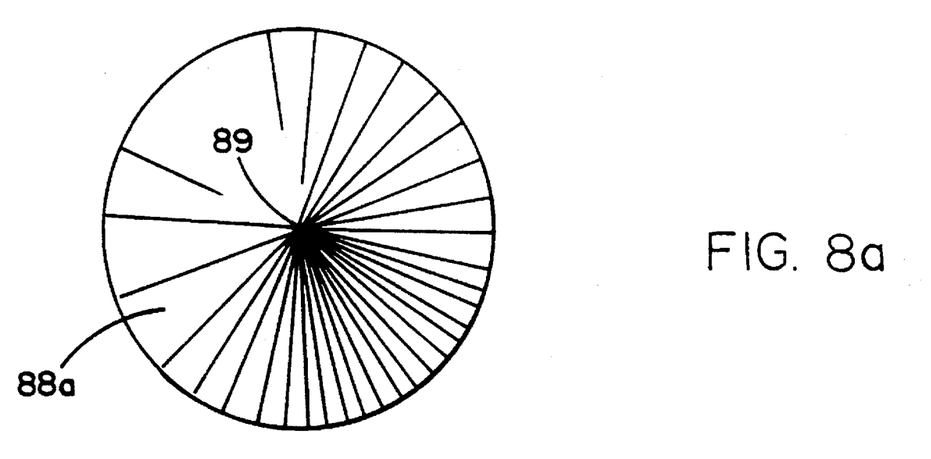
FIGS. 8a and 8b are end views of the FIG. 4 ATR element, FIG. 8a illustrating a conical tip, and FIG. 8b an inverted "roof-top" tip.
Figure 8B:
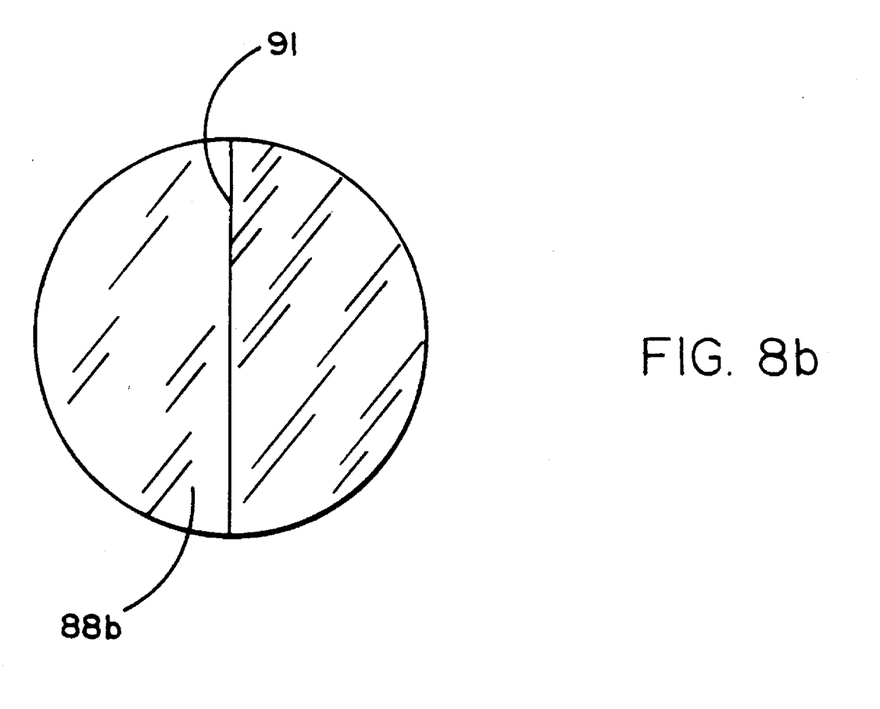

FIG. 8a is a plan view of a conical tip 88a of an ATR element. The apex of the cone is at 89. FIG. 8b is a plan view of a roof-top shaped tip 88b of an ATR element. The ridge (edge) of the roof-top is at 91.

The remaining figures show FTIR spectrometer systems in which the sensing element (probe) of FIG. 4 may be incorporated. The intention is to provide flexibility in positioning the probe relative to the FTIR spectrometer and other elements of the optical system. Two different systems, out of many possibilities, are illustrated. A significant concept in both of the illustrated systems is use of collimated radiation traveling through a relatively large diameter light pipe between the beamsplitter and the probe. Since the transmission losses decrease rapidly as light pipe diameter is increased, this approach greatly increases the length of light pipe that can be used between the beamsplitter and the probe.

Figure 5:
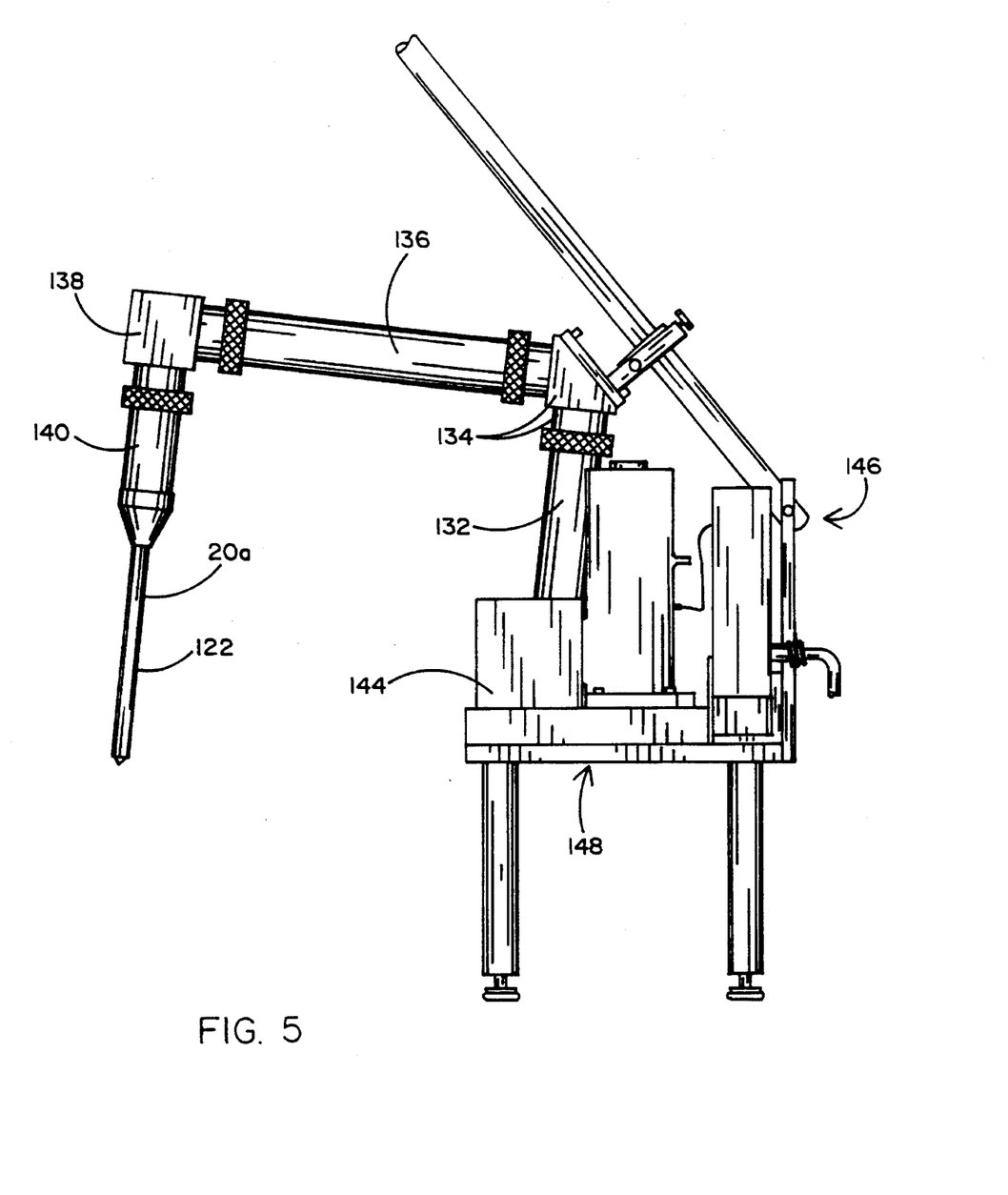
FIG. 5 and 6 are side and front views, respectively, of a spectrometer system incorporating the novel probe disclosed in FIG. 4.
Figure 6:
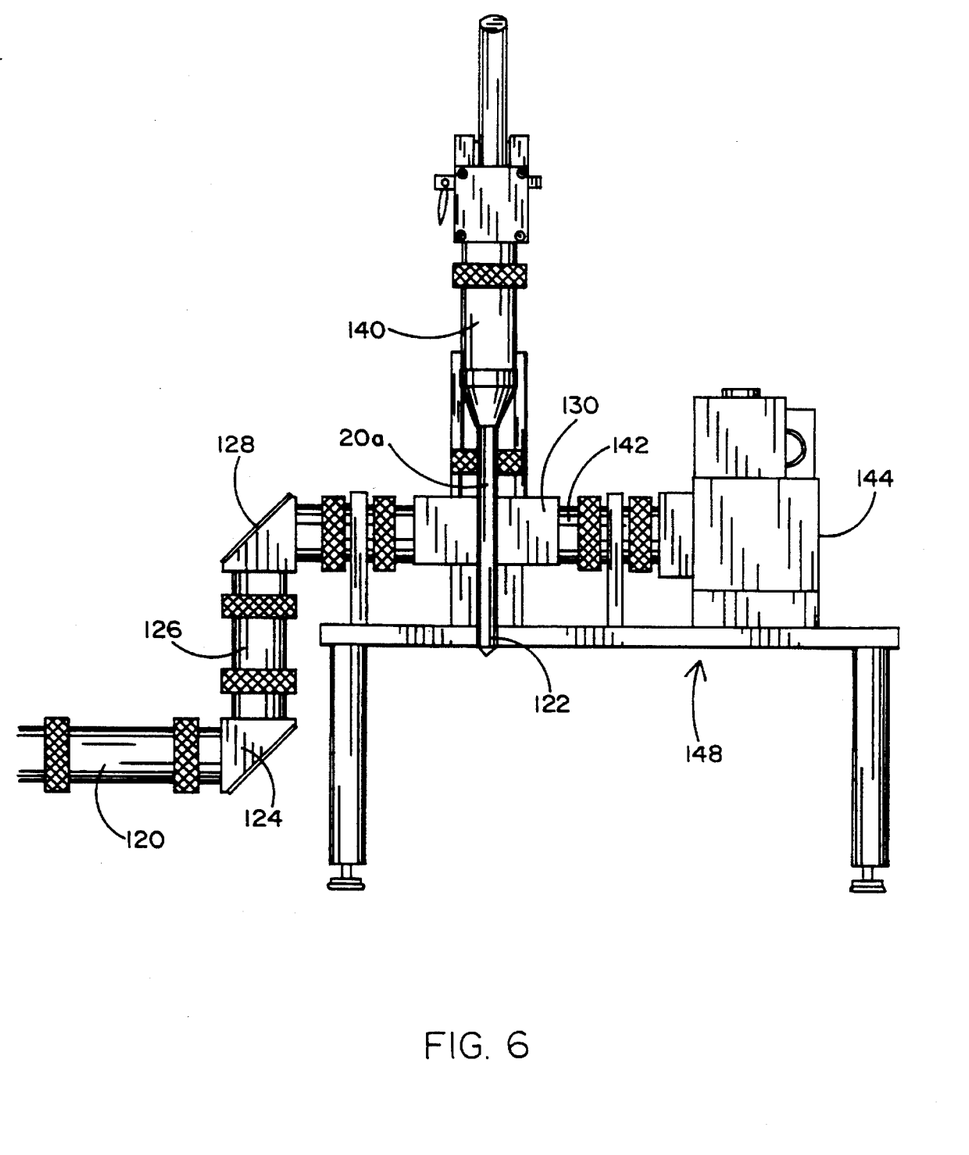

One spectrometer system is shown in FIGS. 5 and 6. This system employs the collimated beam that is provided via a side port on most FTIR spectrometers. Light pipes are shown, having a 32 mm inner diameter. The preferred light pipes are those disclosed in common assignee U.S. Pat. No. 5,054,869, which are referred to as Axiot™ conduits or Axiot transfer optics. As seen in FIG. 6, an Axiot conduit 120 carries post-interferometer collimated radiation toward a sensing head 122, of the type disclosed in FIG. 4. Conduit 120 is attached to a fitting 124 housing a right-angled mirror, which is attached to another Axiot conduit 126. Another mirror-containing fitting 128 causes radiation to be reflected into a beamsplitter assembly 130. The beamsplitter reflects up to one-half of the incoming radiation in an upward direction (in the figure).

Use of the Axiot transfer optics permits flexibility in locating the sensing head 122 at a distance from beamsplitter 130. As seen in FIG. 5, light reflected by the beamsplitter travels through a conduit 132, a right-angled mirror fitting 134, and a conduit 136, to a fitting 138 containing a parabolic mirror. That mirror directs radiation through a conduit 140 to the sensing head 122.

After the radiation has been modulated in the sensing head (which has been inserted into the sample material), returning radiation travels through conduits 140, 136 and 132 to the beamsplitter 130, which reflects up to one-half of the remaining radiation through a conduit 142 to a detector module 144, which is connected to an electronic data-processing system capable of analyzing the electronic signal resulting from the modulated radiation, in order to obtain information regarding the sample material.

A mounting assembly 146, supported on the table 148 which also supports the detector module 144 and beamsplitter assembly 130, is used to lower the sensing head into sample engagement, and to raise the sensing head from the sample after completion of an experiment.

The preferred practical version of the sensing head 122 incorporates a tube element 20a, leading to the ATR element, which comprises inner and outer tubes. The inner tube preferably has a highly reflective light pipe inner surface. The outer tube should be resistive to chemicals. The use of two tubes facilitates manufacturing of the sensing head, because it provides a mounting shoulder to locate the ATR element.

Figure 7:
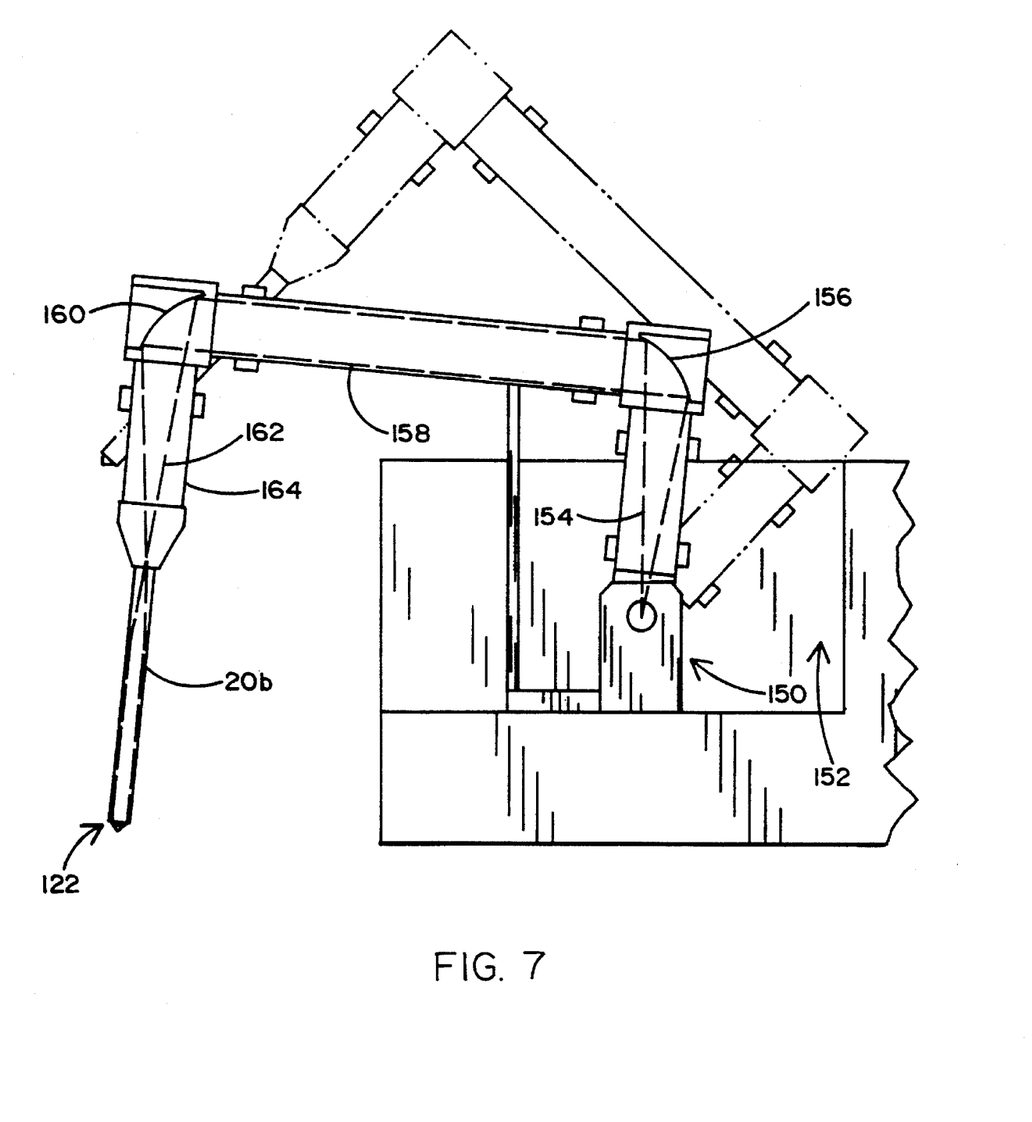
FIG. 7 is a side view showing another version of the spectrometer system incorporating the novel probe.

FIG. 7 shows a second spectrometer system containing the probe of FIG. 4. This design minimizes the number of optical elements needed, by employing a small beamsplitter mounted in the focus of the spectrometer's standard sample compartment. After striking the beamsplitter, the beam diverges to a point where it is reflected by a parabolic mirror. The distance from the beamsplitter to the mirror is set equal to the mirror focal length, so that the radiation emerging from the mirror surface is nominally collimated. From this point on, the system is the same as that shown in FIGS. 5 and 6. In FIG. 7 a beamsplitter assembly 150 is mounted in the existing sample compartment 152 of a spectrometer system. A diverging beam 154 travels to a parabolic mirror 156, which reflects the beam as a collimated beam 158 to a parabolic mirror 160. The converging beam 162 reflected from mirror 160 travels through conduit 164 to enter the tube portion 20b of sensing head 122.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. For use in a spectral analysis system having entering radiation from a source and exiting radiation to a detector, a sample probe structure comprising:

a hollow radiation-confining tube which can be inserted into a sample material, and through which the entering and exiting radiation paths travel; and an ATR element carried by the tube which permits sample material to modulate the radiation which travels through the tube;

said ATR element having (1) a sample-engaging surface which is wedge-shaped in cross-section in order to cause the entering radiation to be reflected back as the exiting radiation, and (2) a back surface which is wedge-shaped in cross-section in order to cause entering radiation which the back surface reflects to separate from the detector-directed exiting radiation.

2. The sample probe structure of claim 1 in which:

the sample-engaging surface and the back surface of the ATR element are each cone-shaped.

3. The sample probe structure of claim 1 in which:

the sample-engaging surface and the back surface of the ATR element are each rooftop shaped.

4. The sample probe structure of claim 1 in which:

the entering radiation is reflected twice at the sample-engaging surface of the ATR element.

5. The sample probe structure of claim 2 in which:

the entering radiation is reflected twice at the sample-engaging surface of the ATR element.

6. The sample probe structure of claim 1 in which:

the wedge-shaped sample-engaging surface has an apex angle which causes the entering and exiting radiation paths in the tube to be parallel.

7. The sample probe structure of claim 2 in which:

the cone-shaped sample-engaging surface has an apex angle which causes the entering and exiting radiation paths in the tube to be parallel.

8. The sample probe structure of claim 7 in which:

the tube has an axis of symmetry parallel to the entering and exiting radiation paths.

9. The sample probe structure of claim 7 in which:

the ATR element has an axis of symmetry parallel to the entering and exiting radiation paths.

10. The sample probe structure of claim 7 in which:

the axis of symmetry of the tube and the axis of symmetry of the ATR element are co-linear.

11. A spectral analysis system comprising:

a source of radiation to be used in analyzing a sample material;

a radiation detector which receives post-sample radiation for analysis;

a radiation-directing sensing head which can be inserted into the sample material for material analysis;

a beamsplitter which reflects entering source-supplied radiation into the sensing head, and reflects exiting sample-modulated radiation to the detector;

the sensing head comprising a radiation-confining tube and an ATR element which is carried by the tube and which enters the sample material;

the ATR element providing sample-engaging surfaces at which the radiation (a) is partially absorbed by the sample, and (b) is redirected so as to exit the sensing head on a path substantially parallel to the path of the entering radiation; and the ATR element causing entering radiation reflected by its entering surface to be so directed that it is not substantially reflected by the beamsplitter toward the detector.

12. The spectral analysis system of claim 11 in which:

the radiation entering surface of the ATR element is wedge-shaped in cross section.

13. The spectral analysis system of claim 11 in which:

the radiation entering surface of the ATR element is a convex cone.

* * * * *